US008354266B2

(12) United States Patent
Li et al.

(10) Patent No.: US 8,354,266 B2
(45) Date of Patent: Jan. 15, 2013

(54) METHOD FOR PRODUCING EXTRACELLULAR MULTI-ENZYME COMPLEXES IN HOST CELLS

(75) Inventors: Wen-Hsiung Li, Taipei (TW);
Ming-Che Shih, Taipei (TW);
Chieh-Chen Huang, Taichung (TW);
Jui-Jen Chang, Kaohsiung (TW);
Cheng-Yu Ho, Taoyuan County (TW)

(73) Assignee: Academia Sinica, Taipei (TW)

( * ) Notice: Subject to any disclaimer, the term of this patent is extended or adjusted under 35 U.S.C. 154(b) by 95 days.

(21) Appl. No.: 12/621,805

(22) Filed: Nov. 19, 2009

(65) Prior Publication Data
US 2011/0117630 A1 May 19, 2011

(51) Int. Cl.
*C12N 1/21* (2006.01)
*C12N 15/63* (2006.01)

(52) U.S. Cl. ................ 435/252.31; 435/262; 435/320.1; 435/264

(58) Field of Classification Search .................. None
See application file for complete search history.

(56) References Cited

U.S. PATENT DOCUMENTS

| 7,931,784 B2* | 4/2011 | Medoff ..................... 204/157.63 |
| 7,932,054 B2* | 4/2011 | Adney et al. ................. 435/68.1 |
| 2003/0027298 A1* | 2/2003 | Bott et al. ....................... 435/183 |
| 2006/0105442 A1* | 5/2006 | Wu et al. ........................ 435/161 |
| 2009/0035811 A1* | 2/2009 | Kohda et al. ..................... 435/41 |
| 2010/0304405 A1* | 12/2010 | Fox et al. ........................ 435/7.4 |
| 2011/0097769 A1* | 4/2011 | Del Cardayre et al. ....... 435/134 |
| 2011/0236943 A1* | 9/2011 | Girbal et al. ................... 435/161 |
| 2011/0306105 A1* | 12/2011 | Chen et al. ..................... 435/165 |

FOREIGN PATENT DOCUMENTS

| FR | 2748479 | * | 5/1996 |
| WO | 2008/100251 | * | 8/2008 |

OTHER PUBLICATIONS

Tamaru, Yutaka e tal, Journal of Bacteriology, 2000, vol. 182(20), pp. 5906-5910, A Large Gene Cluster for the *Clostridium cellulovorans* Cellulosome.*
Han et al, Journal of Bacteriology, vol. 185(8), pp. 2520-2527, Transcription of *Clostridium cellulovorans* cellulosomal cellulase and hemicellulase Genes.*
Zverlov, V V et al, Proteomics, 2005, vol. 5, pp. 3646-3653, Functional subgenomics of *Clostridium thermocellum* cellulosomal genes: Identification of the major catalytic components in the extracellular complex and detection of three new enzymes.*
Zerlov, Vladimer V et al, TUM product description, 2005, p. 1.*
Doi, RH et al, Nature Reviews, Microbiology, vol. 2, Jul. 2004, pp. 541-551, Cellulosomes:Plant-cell-wall-degrading enzyme complexes.*
Xu, Qi et al, Journal of Bacteriology, vol. 185(15), Aug. 2003, pp. 4548-4557, The Cellulosome System of *Acetivibrio cellulolyticus* includes a novel type of adaptor protein and a cell surface anchoring protein.*

(Continued)

*Primary Examiner* — Albert Navarro
*Assistant Examiner* — Ginny Portner
(74) *Attorney, Agent, or Firm* — Occhiuti Rohlicek & Tsao LLP

(57) ABSTRACT

A polycistronic expression cassette encoding proteins necessary for constructing a multi-enzyme complex was developed. Also disclosed herein is a host cell containing this polycistronic expression cassette and uses thereof in degrading biomass.

9 Claims, 5 Drawing Sheets

OTHER PUBLICATIONS

Gold, ND et al, Journal of Bacteriology, 2007, vol. 189(19), pp. 6787-6795, Global View of the *Clostridium thermocellum* Cellulosome Revealed by Quantitative Proteomic Analysis.*

Bayer, Edward A et al, Annu. Rev. Microbiology, 2004, vol. 58, pp. 521-554, The Cellulosomes: Multienzyme Machines for Degradation of Plant Cell Wall Polysaccharides.*

Johnson et al., "Saccharification of Complex Cellulosic Substrates by the Cellulase System from *Clostridium thermocellum*," Applied and Environmental Microbiology, 43(5):1125-1132 (1982).

Schwarz, W.H., "The cellulosome and cellulose degradation by anaerobic bacteria," App. Microbiol. Biotechnol. 56:634-649 (2001).

Mingardon et al., "Exploration of New Geometries in Cellulosome-Like Chimeras," Applied and Environmental Microbiology, 73(22):7138-7149 (2007).

Murashima et al., "Heterologous Production of *Clostridium cellulovorans engB*, Using Protease-Deficient *Bacillus subtilis*, and Preparation of Actove Recombinant Cellulosomes," Journal of Bacteriology, 184(1):76-81 (2002).

Nishizaki et al., "Metabolic Engineering of Carotenoid Biosynthesis in *Escherichia coli* by Ordered Gene Assembly in *Bacillys subtilis*," Applied and Environmental Microbiology, 73(4):1355-1361 (2007).

Wilson, David B., "Cellulases and biofuels," Current Opinion in Biotechnology, 20:295-299 (2009).

Tsunge et al., "One Step Assembly of Multiple DNA Fragments with a Designed Order and Orientation in *Bacillus subtilis* Plasmid," Nucleic Acids Research, 31(21):1-8 (2003).

Bayer et al., "The Potential of Cellulases and Cellulosomes for Cellulosic Waste Management," Current Opinion in Biotechnology, 18:237-245 (2007).

Bayer at al., "Cellulosomes—Structure and Ultrastructure," Journal of Structural Biology, 124:221-234 (1998).

Gold, Nicholas D. and Vincent J.J. Martin, "Global View of *Clostridium thermocellum* Cellulosome Revealed by Quantitative Proteomic Analysis," Journal of Bacteriology, 189(19):6787-6795 (2007).

* cited by examiner (a)

(b)

(c)

(d)

(a)

METHOD FOR PRODUCING EXTRACELLULAR MULTI-ENZYME COMPLEXES IN HOST CELLS

BACKGROUND OF THE INVENTION

Lignocellulosic biomass, rich in cellulose and hemicellulose, has become of particular interest due to its potential use in biofuel production. More specifically, the cellulose and hemicellulose can be hydrolyzed to produce fermentable sugars, which are precursors to ethanol and other biofuels.

One barrier to preparation of biofuels from lignocellulosic biomass is that the fermentable sugars are trapped inside the lignocellulose. Multiple enzymes (e.g., endoglucanase, beta-glucosidase, and cellubiohydrolase) are needed to produce fermentable sugars from cellulose released from biomass via delignification.

There is a need to develop a high order multi-enzyme complex for use in efficient degradation of lignocellulosic biomass to fermentable sugars.

SUMMARY OF THE INVENTION

In one aspect, the present invention features an expression cassette containing a promoter (e.g., a thermo-inducible promoter) operatively linked to a polycistronic nucleotide sequence that encodes a microbial scaffolding protein (e.g., a cellulosomal scaffoldin protein) and at least two enzymes (e.g., at least four, six, eight, or ten). The scaffolding protein contains at least two receptor sites (e.g., at least four, six, nine, or twelve) for binding to ligand sites in the at least two enzymes. Preferably, the polycistronic nucleotide sequence further encodes a microbial cell surface anchoring protein (e.g., a cellulosomal cell surface anchoring protein). The cell surface anchoring protein can contain at least one receptor site (e.g., at least two, four, seven, or ten), for binding to the ligand site in the scaffolding protein. Alternatively, it does not contain any receptor site for binding to the scaffolding protein but is fused with the scaffolding protein.

The enzymes encoded by the polycistronic nucleotide sequence can be cellulosomal enzymes, proteases, nucleases, lipases, laccases, amylases, or a mixture thereof. Each of the enzymes contains a ligand site (e.g., a dockerin domain) for binding to one of the receptor sites in the scaffolding protein. Cellulosomal enzymes refer to the catalytic proteins contained in a cellulosome, including, but are not limited to, cellulase, exoglucanase, endoglucanase (EG, β-1,4-endoglucanase, EC 3.2.1.4), cellubiohydrolase (EXG or CBHs, exo-β-1,4-glucanases, EC 3.2.1.91), β-glucosidase (BGLU, EC 3.2.1.21), xylanase, lichenase (β-1,3-1,4-endoglucanase), mannanase, chitinase, and endopygalactorunase. See Gold et al., J. Bacteriol. 189(19):6787-6795, 2007; Bayer et al., J. Structural Biol. 124:221-234, 1998; Demain et al., Microbiol Mol Biol Rev 69:124-154, 2005; and Wu, ACS Symp. Ser. 516:251-264, 1993. A cellulosomal enzyme can contain a Type-I dockerin domain for binding to a scaffolding protein containing a Type-I cohesin domain.

In one example, the polycistronic nucleotide sequence encodes *C. thermocellum* CipA, CelS, CelK, CelA, XynC, and XynZ proteins. In another example, it further encodes *C. thermocellum* OlpB and CelR proteins.

In a further aspect, this invention features a vector containing the above-described expression cassette or a host cell (e.g., a bacterial cell, a yeast cell, or a mammalian cell) containing the vector. The host cell can be a mesophilic bacterium, e.g., *B. subtilis* or *E. coli*, or a mesophilic yeast.

Also within the scope of this invention is a method of degrading a biomass (e.g., a cellulose-containing biomass) with the host cell described above, which produces a protein complex containing the above-described scaffolding protein, enzymes, and optionally cell surface anchoring protein.

The details of one or more embodiments of the invention are set forth in the description below. Other features or advantages of the present invention will be apparent from the following drawings and detailed description of an example, and also from the appended claims.

BRIEF DESCRIPTION OF THE DRAWINGS

The drawings are first described.

DETAILED DESCRIPTION OF THE INVENTION

Figure 1:
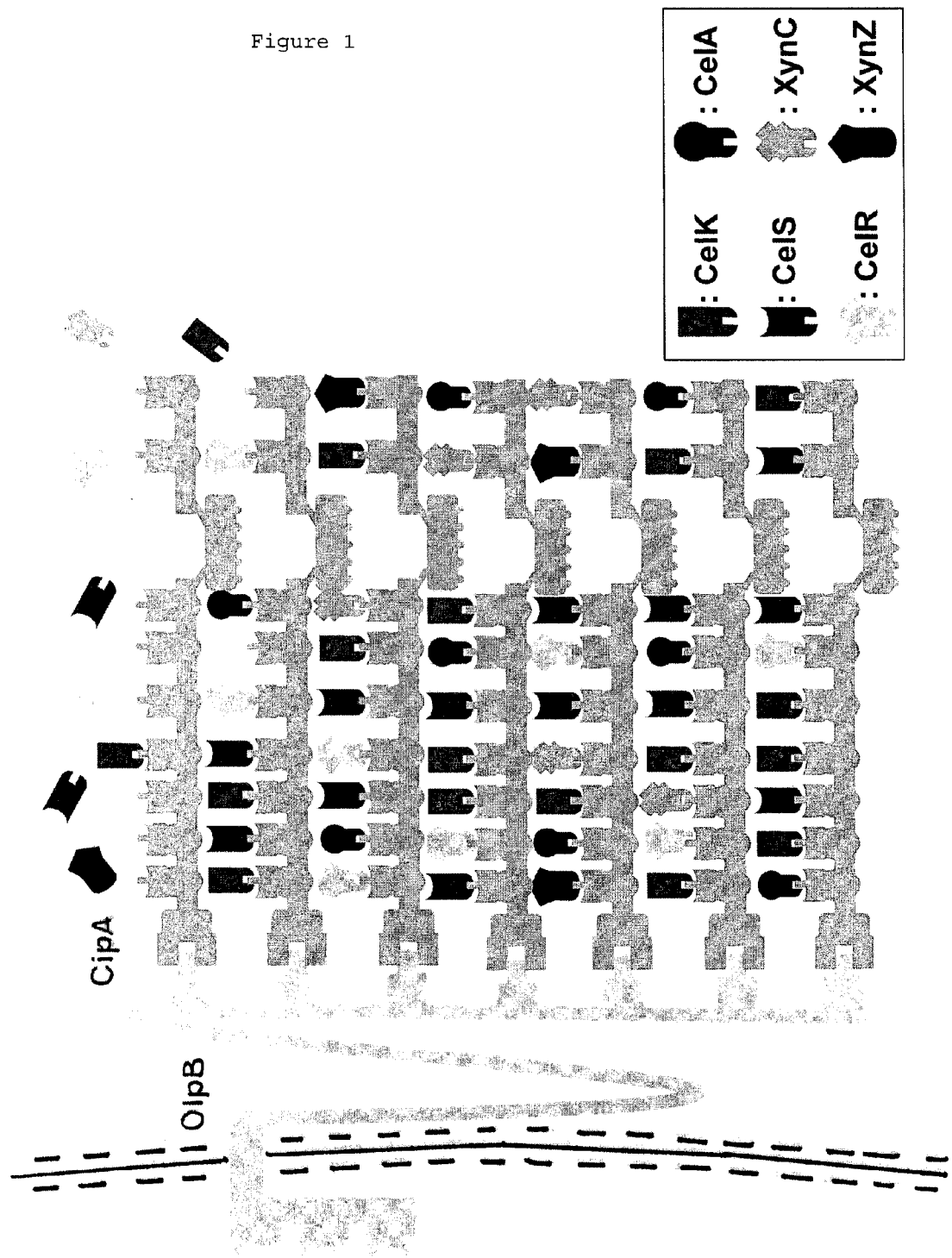
FIG. 1 is a schematic illustration depicting an artificial cellulosome anchored on a cell surface.

Cellulosomes are protein complexes produced by microorganisms for hydrolyzing insoluble polysaccharides, such as celluloses. Typically, a cellulosome contains a cell surface anchoring protein, a scaffoldin protein, and multiple cellulosomal enzymes. The scaffoldin protein, serving as a skeleton of the cellulosome, contains (a) one dockerin domain for binding to a cohesin domain in the cell surface anchoring protein, and (b) multiple cohesin domains each for binding to the dockerin domain in one of the multiple enzymes. The cellulosome can be anchored on cell surfaces via the cell surface anchoring protein. See Gold et al., J. Bacteriol. 189 (19):6787-6795; 2007 and Bayer et al., J. Structural Biol. 124:221-234; 1998.

The present invention relates to preparation of cellulosomes or other structurally similar protein complexes using an operon-type expression cassette for expressing necessary proteins in a suitable host cell. This approach has the following two advantages. First, multiple genes, encoding the multiple proteins, can be introduced into a suitable host cell simultaneously, thereby avoiding multiple cloning processes to introduce each gene sequentially, a time-consuming and technically difficult task. Second, as the positions of the multiple genes in the expression cassette determine their expression levels, switching gene positions can adjust the relative expression levels among these genes.

The expression cassette of this invention includes a suitable promoter in operative linkage with a polycistronic nucleotide sequence that encodes a microbial scaffolding protein, at least two enzymes, and preferably a microbial cell surface anchoring protein. Detailed descriptions of these proteins are provided below:

Microbial scaffolding protein

A microbial scaffolding protein can be any protein found in a microorganism extracellular protein complex (e.g., cellulosome, pilus, flagella, and fimbriae) that provides multiple binding sites for anchoring multiple enzymes in the complex. It contains (1) a ligand site (e.g., a dockerin domain) for binding to the receptor site in a surface anchoring protein, and (2) multiple receptor sites (e.g., cohesin domains) for binding to the multiple enzymes, each of which contains a ligand site (e.g., a dockerin domain). Preferably, the microbial scaffolding protein is a cellulosomal scaffoldin protein containing a dockerin domain (e.g., a Type-II dockerin) for binding to a cohesin domain (e.g., a Type-II cohesin domain) in a cellulosomal cell surface anchoring domain, and multiple cohesin domains (e.g., Type-I cohesin domains) for binding to enzymes that contain dockerin domains (e.g., Type-I dockerin domains). A cellulosomal scaffoldin protein typically also includes one or more carbohydrate-binding modules. Examples of suitable scaffolding protein include, but are not limited to, CipA protein (e.g., from *C. thermocellum*), CbpA protein (e.g., from *C. cellulovorans*), and CipC protein (e.g., from *C. cellulolyticum*).

A microbial scaffolding protein can also be a genetically engineered variant of a naturally-occurring scaffolding protein. Compared to its wild-type counterpart, the variant includes either a heterologous ligand/receptor site(s) or an increased copy number of the receptor site.

A scaffolding protein including a high number of receptor sites (e.g., up to 18) are preferred for preparing high order protein complexes, i.e., containing large numbers of enzyme molecules.

Microbial cell surface anchoring protein

A microbial cell surface anchoring protein, located on cell surfaces, contains a transmembrane domain and an extracellular domain. It can be a naturally-occurring cell surface anchoring protein of a microbial extracellular protein complex. Typically, such a surface protein contains a transmembrane domain and at least one receptor site (e.g., a cohesin domain) for binding to a scaffolding protein that contains a cognate ligand site (e.g., a dockerin domain). Other microbial cell surface proteins, which do not contain a ligand site for binding to a scaffolding protein, also can be used in the protein complex mentioned above. In that case, the cell surface protein can form a fusion protein with a scaffolding protein so as to display the latter on cell surfaces. Examples of a suitable cell surface anchoring protein include, but are not limited to, OlpB protein, SdbA protein, Orf2p protein (e.g., from *C. thermocellum*), ompC protein (e.g., from *E. coli*), ice nucleation protein, and partial ice nucleation protein. See U.S. Pat. Nos. 6,274,345 and 6,071,725.

Alternatively, a microbial cell surface anchoring protein is a genetically engineered variant of a naturally-occurring surface protein that includes a heterologous receptor site or an increased copy number of its endogenous receptor site. For preparing high order protein complex, a surface protein containing a high number of receptor sites (e.g., up to 14) is preferred.

Enzymes

Any enzyme, either naturally occurring or genetically engineered, can be used in making the protein complex mentioned above. To be incorporated into the protein complex, the enzyme includes a ligand site for binding to one of the receptor sites in a scaffolding protein. Many naturally-occurring enzymes, e.g., those from microbial extracellular complexes, contain such ligand sites. If necessary, a ligand site can be inserted into an enzyme of interest by conventional methods.

The types of enzymes chosen for making the protein complex described herein depend on the purpose of the protein complex. For example, when the protein complex is a cellulosome useful in degrading a cellulose-containing biomass, multiple cellulosomal enzymes, as described in Gold et al., 2007, can be used. Such cellulosomal enzymes can be derived from various sources, such as cellulolytic clostridia, (e.g., *C. cellulovorans, C. cellulolyticum*, and *C. papyrosolvens*), *Trichoderma longibrachiatum, Bacteroides cellulosolvens, Acetivibrio cellulolyticusas, Neocallimastix frontalis*, and *Piromyces* spp. 12. When the protein complex is designed for degrading other biomasses, digestive enzymes such as protease, nuclease, amylase, laccases, and lipase, can be used.

In a preferred embodiment, enzymes from a thermophilic microorganism (e.g., *Clostridium thermocellum*) are used. As such enzymes are thermo-stable, protein complexes containing them can exhibit high enzymatic activity at elevated temperature.

To construct the expression cassette mentioned above, DNA fragments encoding the desired proteins can be isolated from their natural sources or prepared by genetic engineering via conventional methods. When PCR is applied to amplify these fragments, high-fidelity polymerases (e.g., KOD, Pfu) are preferred to reduce the possibility of introducing mutations during PCR. The DNA fragments can be ligated downstream to a suitable promoter in a suitable order to form the expression cassette. In one example, the ligation process is performed following the ordered gene assembly methods described in Tsuge et al. J. Biocteriol 183:5453-5458, 2001 and Tsuge et al., Nucleic Acid Res. 31:e133, 2003. In another example, it can be performed by the conventional recombinant technology.

A promoter is a nucleotide sequence containing elements that initiate the transcription of an operably linked nucleic acid sequence. At a minimum, a promoter contains an RNA polymerase binding site. It can further contain one or more enhancer elements which, by definition, enhances transcription, or one or more regulatory elements that control the on/off status of the promoter. Selection of a suitable promoter for constructing the expression cassette depends on the type of host cell to which the expression cassette will be introduced. When *E. coli* is used as the host cell, suitable promoters include, but are not limited to the β-lactamase and lactose promoter systems (see Chang et al., *Nature* 275: 615-624, 1978), the SP6, T3, T5, and T7 RNA polymerase promoters (Studier et al., *Meth. Enzymol.* 185: 60-89, 1990), the lambda promoter (Elvin et al., *Gene* 87: 123-126, 1990), the trp promoter (Nichols and Yanofsky, *Meth. in Enzymology* 101: 155-164, 1983), the tac and trc promoters (Russell et al., *Gene* 20:231-243, 1982), and pCold (see U.S. Pat. No. 6,479,260). When *B. subtilis* is chosen as the host cell, exemplary promoters include Pr promoter, Spol promoter, Tac promoter, and Lad promoter. These promoters can also be used in other bacterial hosts such as *Escherichia coli, Clostridium, Mycoplasma, Lactococcus, Lactobacillus, Vibrio*, and *Cyanobacteria*. Promoters for use in yeast (e.g., *Saccharomyces*) or other fungi (e.g., *Kluyveromyces, Pichia, Aspergillus, Trichoderma*, and *Candida*) include Lac4 promoter, Adh4 promoter, GapDH promoter, Adh1 promoter, Pgk promoter, Aac promoter, Pho5 promoter and Gal7 promoter,.

In a preferred embodiment, an inducible promoter is used in constructing the expression cassette. Such a promoter is active only under a particular condition, e.g., presence of a particular compound (e.g., IPTG or tetracycline) or at a particular temperature (e.g., 40° C. or above).

Inclusion of the desired genes in an expression cassette and their positions as designed can be confirmed by conventional methods, such as gene-specific PCR or restriction enzyme mapping. The expression cassette is then introduced into a suitable host cell for production of a protein complex. When necessary, two or more of the expression cassettes described herein can be delivered into a host cell for expression of multiple proteins. If the desired genes encode thermophilic enzymes, the host cell preferably is mesophilic. Positive clones can be identified by, e.g., antibiotic resistance selection, and confirmed by examining the levels of the expected enzymatic activities. They can then be cultured under suitable conditions allowing expression of the proteins encoded by the genes and assembly of the protein complex.

The protein complex thus prepared, either secreted or anchored on cell surfaces, can be used for various purposes, e.g., for degrading biomass and/or producing biofuels, depending upon the enzymes contained in the complex.

In a multi-enzyme complex, the enzymes, when at an optimal level ratio, act in synergism, thereby exerting high enzymatic activities. As mentioned above, switching the positions of the genes in the expression cassette changes their relative expression levels and consequently, the level ratio of the encoded proteins in the protein complex.

Accordingly, also described herein is a screening method for identifying a multi-enzyme complex that exhibits high enzymatic activity. To practice this method, a library of the operon-type expression cassettes described above, including polycistronic nucleotide sequences encoding the same proteins but in different orders, can be constructed. The cassette library can be introduced into suitable host cells. The transformed host cells that exhibit high enzymatic activities can be identified by, e.g., the methods described in the Example below. The expression cassettes in these identified host cells can be characterized to determine their gene orders. These expression cassettes, when introduced into suitable host cells, can produce multi-enzyme complexes with optimal protein level ratios to achieve synergistic effects among the enzymes.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever. All publications cited herein are incorporated by reference.

Preparation and Characterization of *B. subtilis* Host Cells Expressing High-Order Cellulosomes
Construction of *B. subtilis* cells expressing high-order cellulosomes DNA fragments encoding *Clostridium thermocellum* ATCC 27405 scaffolding protein CipA and cellulosumal enzymes exo-glucosidases CelK and CelS, endo-glucanase CelA, and xylanases XynC and XynZ were amplified by PCR using the KOD-Plus kit provided by TOYOBO CO., LTD., Japan. Scaffolding protein CipA contains one cellulose-binding module (CBM), one surface-layer homologous modules (SLH), and nine Type I cohesin domains.

The PCR products were cloned into plasmid pCR-XL-TOPO using the TOPO XL PCR Cloning Kit (Invitrogen, Calif.) and introduced into *E. coli* host cells following the method described in Mandel and Higa (Mandel and Higa, 1970). DNA plasmids were prepared from positive transformants using the Qiagen Plasmid Midi Kit (Qiagen, Calif.) and subjected to restriction enzyme digestion to produce fragments encoding the above listed cellulosomal proteins. After being extracted from agarose gels, the DNA fragments were used in gene assemble ligation.

An *E. coli/B. subtilis* shuttle vector pGETS 118, described in Tsuge et al., Nucleic Acids Research 31:e133 (2003), was used for cloning the DNA fragments mentioned above. The copy number of this vector in *B. subtilis* is low and can be increased by 1mM isopropyl 1-thio-b-D-galactoside (IPTG). The vector includes Pr promoter, which is thermo-inducible.

The DNA fragments encoding cellulosomal proteins were ligated into shuttle vector pGETS 118 with the order CipA-CelS-CelK-CelA-XynC-XynZ using the ordered gene assembly in *Bacillus subtilis* using the method described in Tsuge et al., *J. Bacteriol* 183:5453-5458 (2003). More specifically, the DNA fragments (equal molar) were mixed with the vector and the ligation reaction was carried out at 16° C. for 30 min using Takara ligation kit Ver. 1 in a 2-fold concentrated buffer [132 mM Tris±HCl (pH 7.6), 13.2 mM $MgCl_2$, 20 mM dithiothreitol, 0.2 mM ATP, 300 mM NaCl, 20%(w/v) polyethylene glycol 6000; Wako pure chemical, Japan]. High molecular weight linear DNA fragments were generated in this ligation reaction.

The linear DNA fragments mentioned above were introduced into a restriction-modification deficient mutant strain *B. subtilis* RM125 and into *B. subtilis* BUSY9166 described in Tsuge et al., 2003 as follows. Competent *B. subtilis* cells were prepared using the two-step culture method described in Anagnostopoulos and Spizizen, *J. Bacteriol.* 1961 81(5):741-6 (1961). A suitable amount of the linear DNA was mixed with 100 ml competent *B. subtilis* cells (in TFII) and incubated at 37° C. for 30 min. 300 ml LB was added to the DNA/cell mixture and the cells were cultured at 37° C. for 1 hour to allow expression of the tetracycline resistance gene carried by the cells. Afterwards, the cultured cells were spread on LB plates containing blasticidin S (500 mg/ml), chloramphenicol (5 mg/ml), erythromycin (5 mg/ml), neomycin (3 mg/ml), spectinomycin (50 mg/ml), and tetracycline (10 mg/ml) for selection of positive transformants.

Clones resistant to tetracycline at 30° C. were further analyzed by enzymatic analysis as follows. Each tetracycline-resistant clone was cultured in a medium (50 ml) containing 1 mM isopropyl 1-thio-b-D-galactoside (IPTG) for 5 hours at 30° C. and then shifted to 42° C. for 3 hours. The supernatant was then collected and concentrated by filtration using an Amicon filter (30 kDa cutoff). The level of UV-irradiated fluorescence in the filtrate was measured to determine the glucanase activity of the clone.

Two clones, Clone 1 and Clone 13, were identified as exhibiting glucanase activity in this study. Gene specific PCR analysis showed that each of the six cellulosomal genes mentioned above was amplified from DNAs prepared from the two clones by gene-specific primers. Restriction enzyme digestion analysis indicated that, in these two clones, the six genes were in the designed order.

Characterization of cellusome-expressing *B. subtilis* cells
(i) Examination of enzymatic activity pGETS-clone1, and pGETS-clone13, as well as *B. subtilis* containing empty vector pGETS (control clone), were grown at 30° C. in the LB medium supplemented with 12.5 ug/ml tetracycline for 6 hours. The cells were then incubated at 42° C. for 5 hours to induce expression of the cellulosomal proteins. Afterwards, the cell cultures were centrifuged at 5000 g for 10 mins. The supernatants were collected and concentrated against an exchange buffer (50 mM Tris, 10 mM $CaCl_2$ and 5 mM DTT pH 6.8) using Viva Flow 50 (10 kDa cut off) (Sartorius, Goettingen, Germany) at 4° C. The cell pellets were also collected, resuspended in PBS, lyzed by sonication (impulse: 3 secs; stop: 2 secs for 12 mins), and then centrifuged at 13200 rpm for 40 mins to remove pellets, resulting in samples containing intracellular proteins ("intracellular samples"). Alternatively, the cell pellets were collected and resuspended in PBS to produce samples containing intact cells.

The protein contents of the supernatants and intracellular samples were determined by the Bradford method. Both samples were subjected to enzymatic activity analysis as follows.

Figure 2:
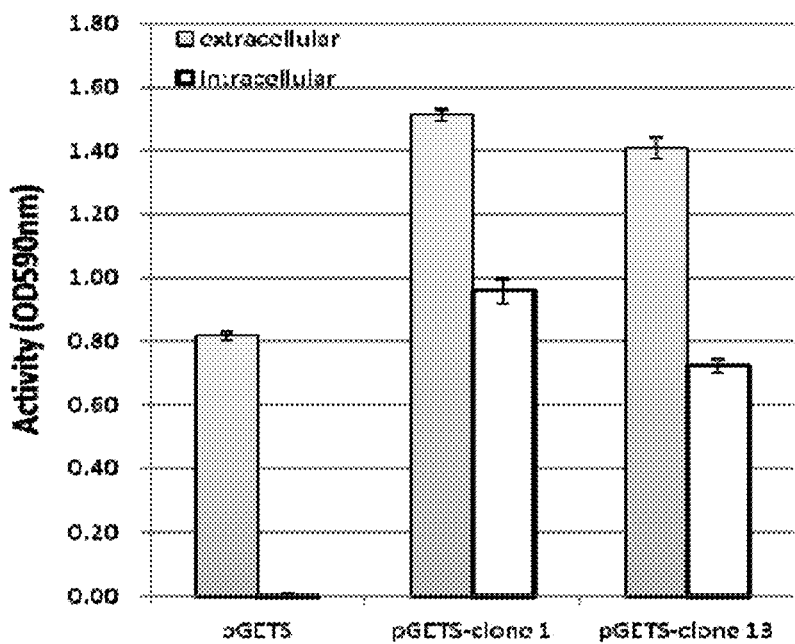
FIG. 2 is a chart showing extracellular and intracellular cellulolytic activity in *B. subtilis* host cells producing a protein complex containing *C. thermocellum* CipA, CelS, CelK, CelA, XynC, and XynZ proteins. (a): endo-glucanase activity determined with Azurin-linked β-glucan (dye CMC) as a substrate; (b) specific endo-glucanase activity, determined by normalizing endo-glucanase activity in a sample against its protein content; (c): total glucanase activity determined with 4-methylumbelliferyl-β-d-cellobioside (MUC) as a substrate; and (d): specific total glucanase activity, which is determined by normalizing total glucanase activity in a sample against its protein content.
Figure 2:
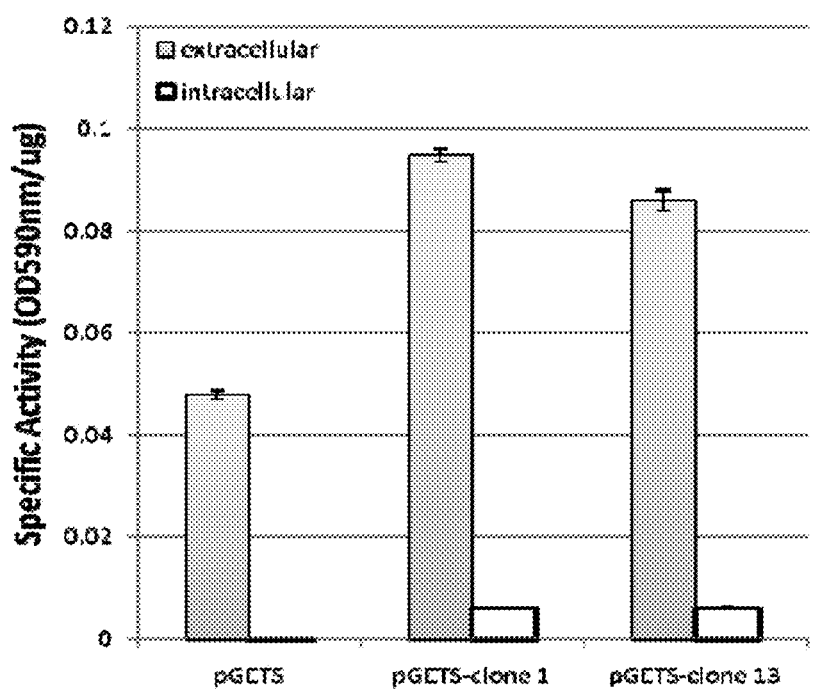
Figure 2:
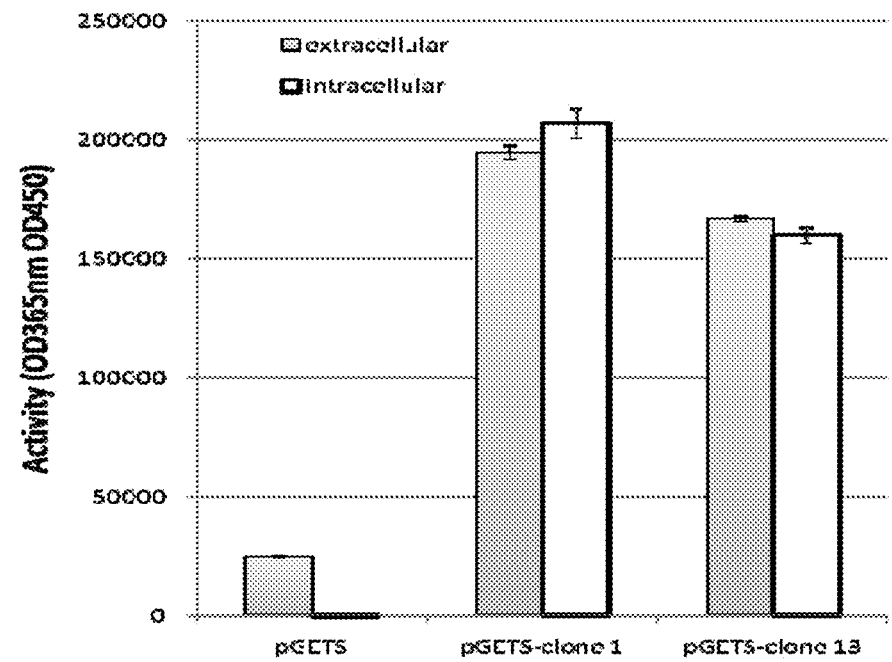
Figure 2:
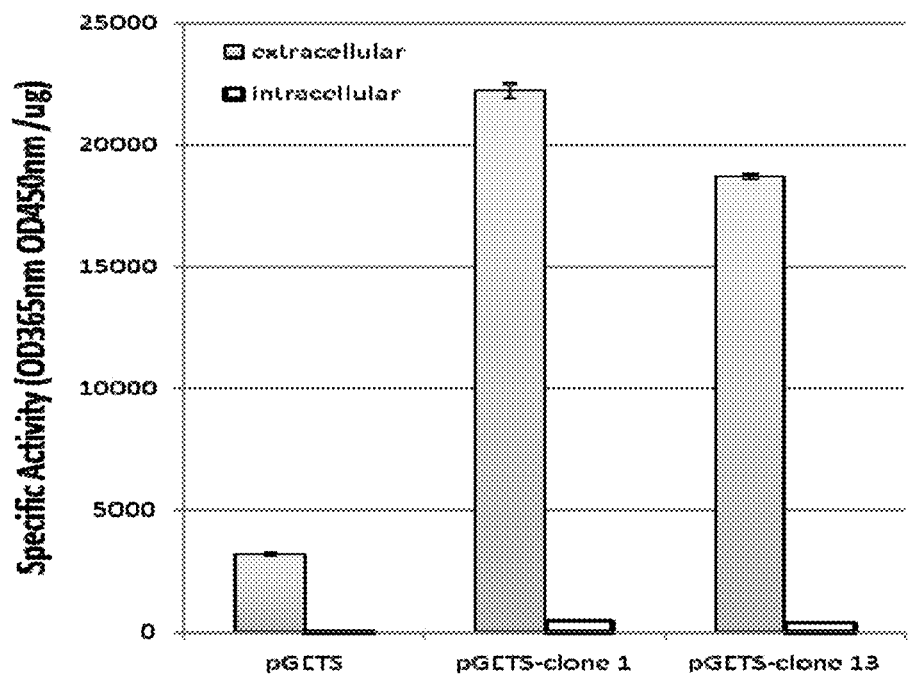

Endo-glucanase activity was determined using Azurine cross-linked (AZCL) -β-glucan (dye CMC) (purchased from Megazyme) as the substrate. The supernatant and intracellular samples mentioned above were incubated with 1% (v/w) dye CMC in 50 mM sodium acetate (pH 5.0) at 60° C. for 3 hours. The absorbance at 590 nm of each sample was then measured. The $OD_{590}$ values correlate with glucanase activity levels. The results indicate that the endo-glucanase activity in the supernatants of Clones 1 and 13 were 2 fold higher than that in the supernatant of the control clone. See FIG. 2(a). On the other hand, significant levels of the endo-glucanase activity were detected in the intracellular samples from Clones 1 and 13, while the endo-glucanase activity was not detectable in the intracellular sample from the control clone. See FIG. 2(a). Relative to the intracellular protein content of the control clone, those of Clones 1 and 13 were found to be significantly elevated, indicating that a certain amount of the exogenous proteins were remained inside the cells as determined by the values of specific activity (enzymatic activity normalized against total protein content). See FIG. 2(b).

To examine the total glucanase activity, both supernatants and intracellular samples were mixed with 4-methylumbelliferyl-β-d-cellobioside (MUC) at a final concentration of 1 mg/ml in 50 mM sodium acetate buffer (pH 5.0) at 60° C. for 3 hours. The enzymatic activity was determined by fluorometry under UV irradiation at 365 nm in 1% $Na_2CO_3$. The results thus obtained show that the glucanase activities observed in the supernatants from Clones 1 and 13 were much higher than that observed in the supernatant from the control clone. See FIG. 2(c). Again, a certain amount of the exogenous proteins were found to be retained inside the cells. See FIG. 2(d).

(ii) Examination of protein complex formation

The formation of cellulosomal protein complexes in Clones 1 and 13 was determined by SDS-PAGE. More specifically, extracellular protein samples prepared from the two clones (with no boiling) were subjected to electrophoresis on a 5-15% (w/v) polyacrylamide gel containing 0.1% SDS. The polyacrylamide gel was then placed on top of an agarose gel containing Xylan or CMC and bubbles between the two gels were removed. The two gels were wrapped with a plastic membrane and incubated at 40° C. for 3 hrs (if the agarose gel contains CMC) or at 60° C. overnight (if the agarose gel contains Xylan). Afterwards, the polyacrylamide gel was separated from the agarose gel, fixed, and subjected to sypro ruby staining The agarose gel was immersed in 1 mg/m1 Congo red for 30-60 mins and then in 1 M NaCl for 10-60 mins. The position on the agarose gel where substrate CMC or Xylan was degraded appears yellow and positions where no degradation occurs appear dark-red. The polyacrylamide gel was also incubated in a solution (pH 5.0) containing 0.2 mg/ml MUC and 50 mM NaOAc at 60° C. and 30 mins to detect its glucanase activity. Degradation of MUC was detected by examining the fluorescence level on the gel at 365 nm.

The results obtained from the above studies showed that both Clones 1 and 13 exhibited extracellular glucanase, xylanase, and β-glucosidase activity.

Proteins on the polyacrylamide gel mentioned above were transferred to a polyvinylidene difluoride membrane (GE) following the method described in Matsudaira, J. Biol. Chem. 262:10035-10038 (1987) or Salinovich and Montelaro, Anal. Biochem. 156:341-347 (1986). The membrane was blocked with PBS containing 5% skim milk, washed, and then incubated with an anti-rCipA antibody (1:5000 dilution) for 16 h at 4° C. After being washed for several times, the membrane was incubated with a HRP-conjugated goat anti-rabbit IgG (1:5000 dilution). After being washed with PBS (pH 7.4), the membrane was incubated with a solution containing NBT/BCIP for signal development. The result indicated that the position of CipA protein in the polyacrylamide gel overlapped with the position where cellulase activity was observed.

Proteins at the position where cellulase activity was observed were extracted from the gel and subjected to protein mass analysis by a 5-15% (w/v) polyacrylamide gel and a two-dimensional DIGE gel electrophoresis. Peptides highly homologous to fragments of CelA, CelK, CelS, CipA, and XynZ proteins were found in this analysis, indicating that these proteins form a protein complex and exhibits the expected enzymatic activity.

(iii) Examination of enzyme thermo-stability

Figure 3:
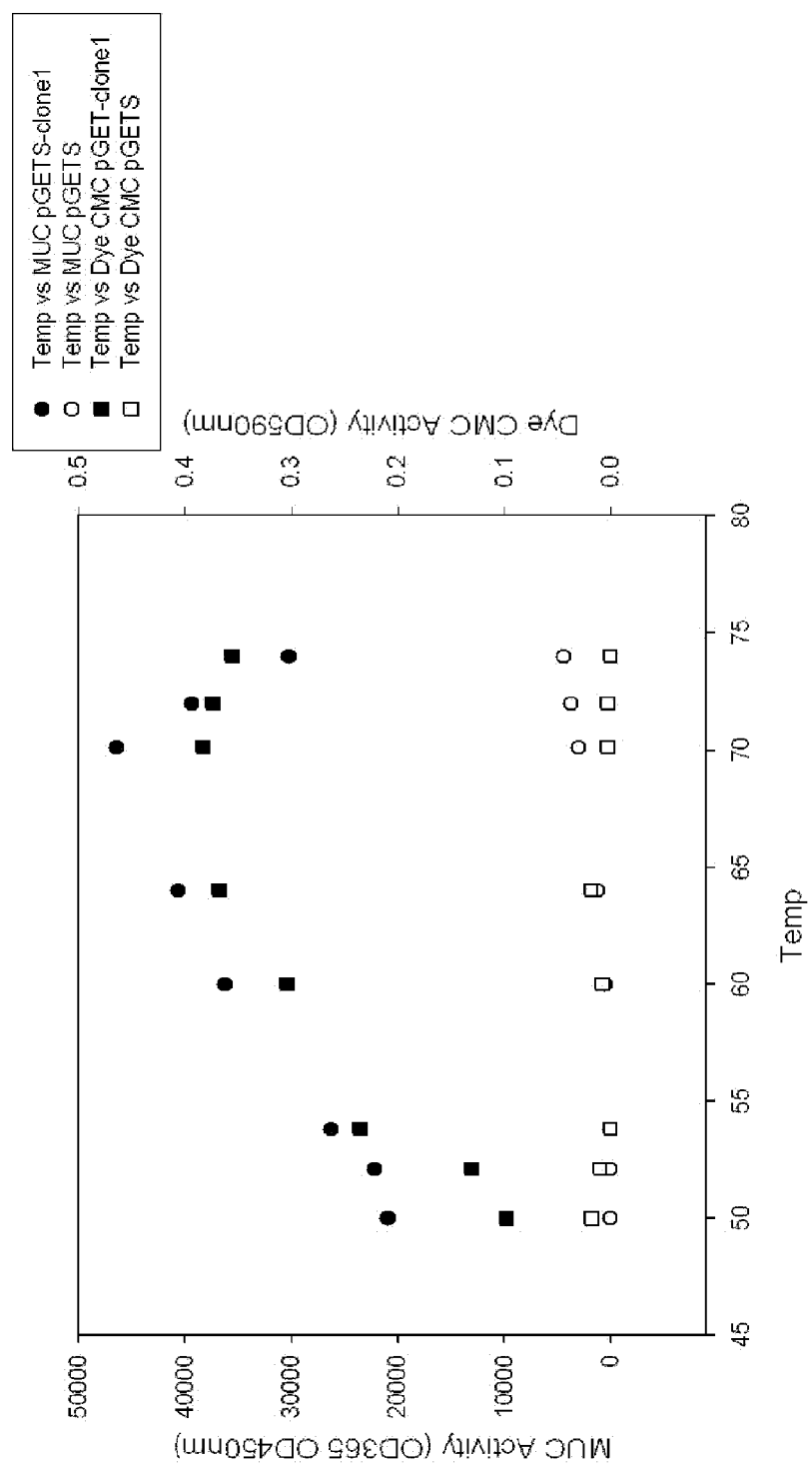
FIG. 3 is a diagram showing thermo-stability of cellulosomal glucanase in a protein complex, produced in *B. subtilis*, that contains *C. thermocellum* CipA, CelS, CelK, CelA, XynC, and XynZ proteins. (a): Glucanase activities of a control *B. subtilis* clone and two *B. subtilis* clones producing the protein complex under different temperatures; and (b): Glucanase activities and protein contents of a control *B. subtilis* clone and two *B. subtilis* clones producing the protein complex under different temperatures.
Figure 3:
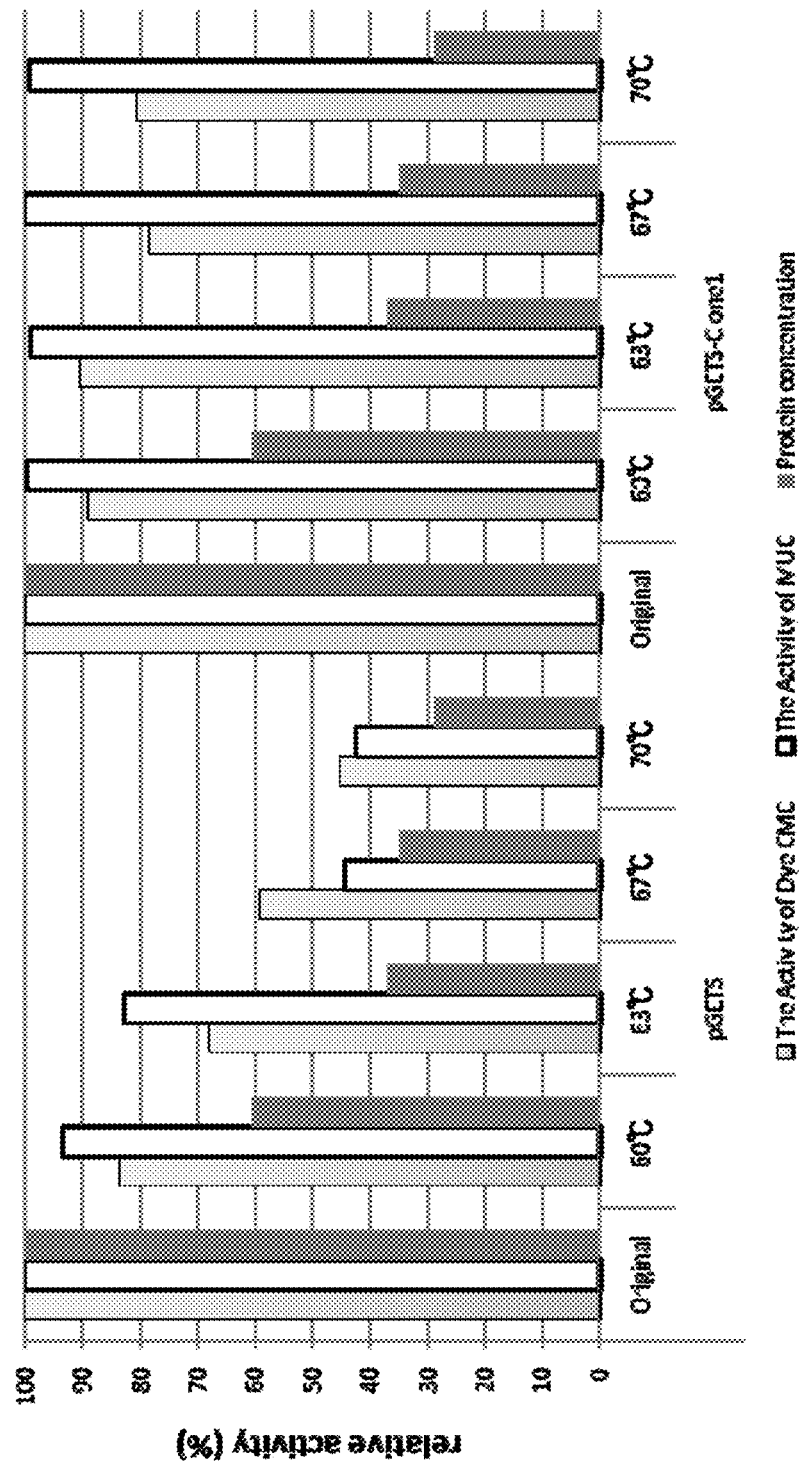

The extracellular cellulolytic activity of Clones 1 and 13 and the control clone was determined at different temperatures following the methods described above. Compared to the control clone, Clones 1 and 13 showed much higher enzymatic activity at temperatures above 50° C. and the differences were greater at higher temperatures. See FIG. 3(a). The extracellular protein contents of all three clones were found to be similar at each testing temperature. See FIG. 3(b). This indicates that the elevated enzymatic activity is due to thermo-stability of the cellulosomal enzymes expressed in Clones 1 and 13.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An expression cassette comprising a promoter operatively linked to a polycistronic nucleotide sequence including *C. thermocellum* genes, wherein the genes are in the order of cipA, celS, celK, celA, xynC, and xynZ.

2. The expression cassette of claim 1, wherein the promoter is a thermo-inducible promoter.

3. The expression cassette of claim 2, wherein the promoter is a lambda phage right (Pr) promoter.

4. A vector comprising the expression cassette of claim 1.

5. A host cell comprising the expression cassette of claim 1.

6. The host cell of claim 5, wherein the host cell is *mesophilic*.

7. The host cell of claim 6, wherein the host cell is a *B. subtilis*.

8. A method for degrading a biomass, comprising culturing the host cell of claim 5 under conditions that allow expression of the proteins encoded by the *C. thermocellum* genes, and contacting a biomass with the cultured host cell.

9. The method of claim 8, wherein the biomass contains cellulose.

* * * * *